(12) United States Patent
Klein et al.

(10) Patent No.: US 9,445,902 B2
(45) Date of Patent: Sep. 20, 2016

(54) PLATFORM FOR SOFT TISSUE ATTACHMENT

(75) Inventors: Robert W. Klein, Orangeburg, NY (US); Aaron Essner, Bloomingdale, NJ (US); Anthony P. Napolitano, Chappaqua, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 250 days.

(21) Appl. No.: 13/504,204

(22) PCT Filed: Oct. 20, 2010

(86) PCT No.: PCT/US2010/053314
§ 371 (c)(1),
(2), (4) Date: Jun. 11, 2012

(87) PCT Pub. No.: WO2011/056422

PCT Pub. Date: May 12, 2011

(65) Prior Publication Data

US 2012/0253474 A1    Oct. 4, 2012

Related U.S. Application Data

(60) Provisional application No. 61/257,580, filed on Nov. 3, 2009.

(51) Int. Cl.
*A61F 2/30* (2006.01)
*A61F 2/28* (2006.01)
(Continued)

(52) U.S. Cl.
CPC ............. *A61F 2/30756* (2013.01); *A61F 2/28* (2013.01); *A61L 27/047* (2013.01); *A61L 27/56* (2013.01);
(Continued)

(58) Field of Classification Search
CPC .... A61F 2/08; A61F 2/30; A61F 2002/2835; A61F 2002/30004; A61F 2002/30011; A61F 2002/30013; A61F 2002/30766

USPC ......... 623/14.12, 23.51, 23.52, 23.53, 23.76, 623/16.11
See application file for complete search history.

(56) References Cited

U.S. PATENT DOCUMENTS

2007/0142914 A1 * 6/2007 Jones et al. ................ 623/14.13
2007/0179607 A1   8/2007 Hodorek et al.
(Continued)

FOREIGN PATENT DOCUMENTS

WO    2009092082 A2    7/2009

OTHER PUBLICATIONS

International Search Report and Written Opinion, PCT/US2010/053314, Dated Dec. 13, 2010.

*Primary Examiner* — Bruce E Snow
(74) *Attorney, Agent, or Firm* — Lerner, David, Littenberg, Krumholz & Mentlik, LLP

(57) ABSTRACT

One embodiment of the implant comprises a porous metal bone ingrowth portion (14) having a first side connected to a high density or solid (fully dense) metal portion (16) which in turn has an opposite side connected to a porous metal soft tissue ingrowth portion (12) thus forming a sandwich structure with the high density or fully dense portion in the middle. The implant may be made of a resorbable material such as an alloy of magnesium. Alternately, the alloy can be selected from the group consisting of calcium, iron, yttrium and lithium. The porous metal soft tissue ingrowth portion (12) has porosity characteristics allowing cartilage to interdigitate with the pores and extend outwardly beyond the platform of the metal surface towards a joint capsule. The solid or fully dense intermediate layer 16 may have some porosity, however that porosity prevents either bone tissue or cartilage tissue from migrating therethrough.

4 Claims, 2 Drawing Sheets

(51) Int. Cl.
*A61L 27/04* (2006.01)
*A61L 27/56* (2006.01)

(52) U.S. Cl.
CPC ........... *A61F 2002/30011* (2013.01); *A61F 2002/30062* (2013.01); *A61F 2002/3092* (2013.01); *A61F 2002/30766* (2013.01); *A61F 2002/30962* (2013.01); *A61F 2210/0004* (2013.01); *A61F 2250/0023* (2013.01); *A61F 2310/00041* (2013.01); *A61L 2430/02* (2013.01)

(56) References Cited

U.S. PATENT DOCUMENTS

| | | |
|---|---|---|
| 2008/0097577 A1 | 4/2008 | Atanasoska et al. |
| 2008/0140199 A1 | 6/2008 | Briest |
| 2008/0312736 A1* | 12/2008 | Mueller et al. ............ 623/1.46 |
| 2009/0048660 A1 | 2/2009 | Adden |
| 2009/0076624 A1 | 3/2009 | Rahaman et al. |
| 2009/0081313 A1* | 3/2009 | Aghion et al. ............... 424/641 |
| 2010/0036492 A1 | 2/2010 | Hung et al. |

* cited by examiner

PLATFORM FOR SOFT TISSUE ATTACHMENT

CROSS-REFERENCE TO RELATED APPLICATION

The present application is a national phase entry under 35 U.S.C. §371 of International Application No. PCT/US2010/053314 filed Oct. 20, 2010, published in English, which claims priority from U.S. Provisional Patent Application No. 61/257,580 filed Nov. 3, 2009, all of which are incorporated herein by reference.

BACKGROUND OF THE INVENTION

The present invention relates to a device having two different porous surfaces attached directly or indirectly to one another and a method for forming the same.

The present application is particularly directed toward a method of forming porous or partially-porous metallic structures having different porosities for bone ingrowth and soft tissue ingrowth or attachment.

One method of producing the different porous structures uses rapid prototyping to produce low density three-dimensional structures. This is useful in applications where porous and partially-porous metallic structures, and more particularly metal porous structures with interconnective porosity are advantageous for use. In addition, composite structures of metal and porous ceramics or porous polymer can be used.

Many structures, especially in the medical arts, require two different surfaces, each adapted for their own purposes. Along this line, a structure may have a first surface which needs to be porous for tissue in-growth and a second surface which could be adapted to be a bearing surface. See for example U.S. Patent Publication No. 2007/0142914, the disclosure of which is incorporated herein by reference. Further, the first surface or portion may include different layers having different gradients of porosity. For example, the first surface may include an outer region having a porosity of approximately 80%. As you move normal with regard to the first surface the porosity may alter such that the porosity is increased or in a preferred embodiment, the porosity decreases even until the porosity is almost zero. Of course, the present invention contemplates a situation where the porosity changes from position to position depending on the requirements of the device.

BRIEF SUMMARY OF THE INVENTION

The present invention is a composite system that may become a permanent metallic structure attached to tissue or tissues, including, tendon, ligament, cartilage, muscle or bone or may be at least partially resorbable. The system may utilize a number of features that restore initial function and promote tissue healing including:
- porous metal for tissue in-growth and or ongrowth
- additional metallic structures (solid or reduced porosity) for stiffness and strength as well as composites of porous polymers or porous ceramics
- structures that allow transport and diffusion of nutrients or blood supply
- flexible structures that can be affixed to tendon, ligament, or muscle with sutures, darts, pins, staples, screws or other mechanical means
- "bio-material" that will act as a matrix for formation of appropriate soft tissue and facilitate biological attachment to the porous metal—this material can contain live cells, and/or appropriate growth factors or bioactive molecules to stimulate cells once it has been implanted
- material for attachment to the muscle or bone to convey blood supply
- structures to interface with instruments for initial implantation
- structures to interface with an orthopedic implant The load bearing capability of the metallic support structure and tissue may be accomplished by formation of a load bearing soft tissue with viable cells in vitro and by re-enforcement of the tissue with permanent or absorbable flexible structures that limit stretching and can be fixed to the soft tissue with sutures or some other surgical or mechanical method.

Promoting and sustaining growth of appropriate tissue for long term function of the soft tissue being repaired—this may be done by the addition of factors such as proteins, cytokines or other suitable bioactive molecules to a suitable matrix or gel biomaterial to promote growth and formation of appropriate soft tissue. It is also desirable to design the metallic structure so that it can be attached to tissues with good blood supply such as muscle or bone. This may also be accompanied by insuring that the tissue and metallic support structure have adequate transport properties to support cells without direct blood supply (e.g. chondrocytes).

The system can achieve long term anchoring of the soft tissue to bone, to part of a joint replacement, or to both. This may be accomplished by having features for initial fixation in bone as well as porous regions for bone in-growth or on-growth. Implants that attach soft tissue to bone may have interconnected porosity between the bone interfacing regions and the soft tissue interfacing regions to promote formation of a physiological type bone/soft tissue interface. For segmental implants, where there is no bone, the system would be permanently attached to the implant at an appropriate functional location. A porous surface would not be needed where the system is fixed to the segmental implant.

The present invention addresses the issue of attaching soft tissue to bone or attaching soft tissue to an implant. Historically, bone has been attached to bone and soft tissue has been attached to soft tissue. Ligaments and tendons then remain attached to bone can be surgically attached to bone or an implant with success. Results are often less successful when there is no bone on the ligament or tendon. Tendon repairs have been attempted by directly attaching the tendon to bone or implants using sutures. There are sports medicine products consisting of sutures on anchors that go into bone. There are segmental joint replacements with suture holes or mechanical clamps in combination with porous in-growth surfaces to attach tendons.

Ligament repairs are typically done by suturing ligament to ligament or by substituting ligament with bone attached at both ends. Soft tissues have been attached to other soft tissues (e.g. ligament shortening) using a variety of suturing or stapling techniques. Biological scaffolds have been used to grow tissue in laboratory settings as well as in animals. There are also products based on biological matrices, but their strength is limited and it becomes lower as the matrix is broken down by the live cells.

The present invention is an improvement over previous techniques for tendon or ligament attachment in that the metallic structure provides initial load bearing capability that remains intact through the tissue healing process. Porous metals have been used for bone in- or on-growth and soft tissue in- or on-growth. The porosity of the metallic structure allows for long term tissue integration and fixation. The flexible structures allow for attachment of the soft tissue to the implant using conventional surgical techniques, and can transfer loads that occur during rehabilitation without comprising the length of the reconstruction. The matrix promotes soft tissue healing which is what provides long term stability and function to the reconstruction.

The present invention is an improvement over previous cartilage repairs that have been done using biological materials with poor mechanical properties. The present invention helps with mechanical conditioning of the cells when forming the cartilage in a laboratory or biological manufacturing type setting. The invention is distinguished by having a porous structure to accommodate cartilage growth, a porous structure to accommodate bone growth, and structural metal between the porous metal layers. This metal can prevent vascular structures from growing into the cartilage, allow diffusion of nutrients to the chondrocytes, simplify application of the biological material to the cartilage accommodating layer, reinforce the metal structure to reach a desired stiffness or strength, and provide a place for the device to be mechanically fixed to an instrument for implantation. In the case of a bone to tendon connection the porous structure can be designed to allow the vascular structure to cross the denser structure by making it have porosity In one embodiment chondrogenic cells (chondrocytes, stem cells, or other cartilage forming cells) may be suspended within a hydrogel matrix which interdigitates with the pores of the cartilage growth structure and extends beyond the surface of the cartilage growth structure at a height that approximates the native cartilage to be replaced. The hydrogel matrix may be remodeled by the cells in vitro or in vivo to create a living cartilage replacement with mechanical properties that approach native cartilage. This construct may be created by suspending live chondrogenic cells within a pre-gelled liquid hydrogel precursor, dipping the porous metal substrate into the liquid to such a depth as to fill the pores of the cartilage ingrowth structure, and allowing the liquid to gel.

The present invention utilizes a unique combination of permanent and tissue forming materials that can be used with conventional surgical techniques for tissue reconstruction.

In another embodiment the porous metal substrate may be created from a bioresorbable metal alloy such as magnesium alloy. Slowly degrading metal alloys would provide long term mechanical strength and stability, but would ultimately be replaced by native tissue. Magnesium is known to degrade in the body and release Mg ions. Mg ions are essential to human metabolism and are naturally found in bone tissue. Furthermore, magnesium provides a good bone growth surface and may even stimulate new bone growth. Li et al. recently investigated the use of several magnesium-calcium alloys for use in bone implants. (The development of binary Mg—Ca alloys for use as biodegradable materials within bone. Biomaterials 29, 2008. 1329-1344). This study demonstrated the feasibility of implanting biodegradable magnesium alloys into bone using in vitro and in vivo models. Other bioresorbable metals that are naturally found in the body such as iron may also be used. These metals may also be alloyed with small amounts of other metals such as silver and zinc which are known to have antimicrobial and pro-immune properties respectively.

In one embodiment, the present invention relates to a method of forming an implant having a porous soft tissue ingrowth structure and a porous bone ingrowth structure. The method may include depositing a first layer of a metal powder onto a substrate. Next, a laser beam scans over the powder so as to sinter the metal powder at predetermined locations. At least one layer of the metal powder may be deposited onto said first layer while repeating the laser scanning step for each successive layer until a predetermined porous structure having a first surface and a second surface is constructed.

The predetermined structure may include an outer layer, an intermediate layer and an inner layer, the outer layer and the inner layer being relatively porous and the intermediate layer being relatively dense to separate the two porous layers. The outer layer has a porosity approximately between 60% to 80% and the inner layer has a porosity approximately higher than 80%. The outer layer may have a pore size distribution in the range of 80 µm to 800 µm and the inner layer may have a pore size distribution higher than approximately 800 µm.

The predetermined structure may have a gradient porosity. The gradient porosity of the predetermined structure may include a first layer that is substantially porous for bone tissue, a second layer that is substantially non-porous, a third layer that is substantially porous for tissue ingrowth such that the soft tissue cannot grow into the bone tissue area.

The present invention also includes a medical implant including a metal insert having a bone ingrowth structure, an intermediate structure and a second porous structure for soft tissue ingrowth, the bone ingrowth structure having a porosity sufficient to promote bone ingrowth and the soft tissue ingrowth structure promotes tissue ingrowth. The implant also includes a bearing surface formed from a polymer material, the bearing surface being attached to the bearing support structure. The intermediate structure has a porosity sufficient to inhibit the bone or soft tissue from migrating through the porous structure to the other ingrowth structure. The intermediate structure may be designed to facilitate a specific stiffness characteristic to an overall construct and/or include two barrier layers and a bridging section.

One embodiment of the implant comprises a porous metal bone ingrowth portion having a first side connected to a high density metal portion which high density metal portion in turn has an opposite side connected to a porous metal soft tissue ingrowth portion thus forming a sandwich structure with the high density or fully dense (solid) portion in the middle. The implant may be made of a resorbable material such as an alloy of magnesium. Alternately, the alloy can be selected from the group consisting of calcium, iron, yttrium and lithium. The porous metal soft tissue ingrowth portion has porosity characteristics allowing cartilage to interdigitate with the pores and extend outwardly beyond the metal surface towards a joint capsule. The solid or fully dense intermediate layer may have some porosity, however that low porosity prevents either bone tissue or cartilage tissue from migrating therethrough.

DETAILED DESCRIPTION

The present invention relates to a method of forming two porous or partially porous metallic structures attached directly or indirectly thereto. The structures are particularly but not exclusively applicable for use in the art of soft tissue/bone interlock structures for medical implants and prosthesis.

In one embodiment the method makes use of laser technology or any other high energy beam by employing a variety of scanning strategies.

Typical metal and metal alloys employed in such laser technology include stainless steel, cobalt chromium alloys, titanium and its alloys, tantalum and niobium, all of which have been used in medical device applications. In addition resorbable metal alloys such as magnesium alloys containing members selected from the group consisting of calcium, iron, lithium and yttrium can be used. The present invention can be used for such medical device applications where bone and/or soft tissue interlock with the component is required, or where a controlled structure is required to more closely match mechanical properties of the device with surrounding tissue.

The bone ingrowth structure, as well as the soft tissue ingrowth structure and intermediate structure may be constructed using a direct laser remelt process as, for example, described in U.S. Pat. No. 7,537,664, filed Nov. 7, 2003 entitled "Laser-Produced Porous Surface," and U.S. Patent Publication No. 2006/0147332, filed Dec. 30, 2004, entitled "Laser-Produced Porous Structure," the disclosures of which are incorporated herein by reference.

Figure 1:
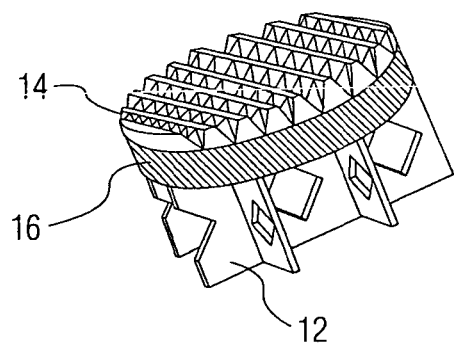
FIG. 1 is an embodiment of an implant having a bone ingrowth structure and a soft tissue ingrowth structure.

As shown in FIG. 1, in one embodiment of the present invention, the bone ingrowth structure 14 is approximately 1.1 mm thick and has a porosity of approximately between the range of 70% to 80%. The intermediate structure 16 is approximately 0.1 mm thick and is substantially fully dense. The soft tissue ingrowth structure is approximately 0.8 mm thick.

The bone ingrowth structure 14 may be prepared by populating the volume of the structure with a single unit repeating cell using propriety software. A single unit cell 110 and the corresponding porous layer are shown in FIG. 1C and 1D. The single cell 110 used is a unit cell octahedron structure having a length of 800 µm with vertical pillars on each corner. When tessellated, these cells produce porous structures having a porosity of approximately 80% with full interconnected porosity and mean pore sizes between 100 µm and 400 µm.

The intermediate structure 16 is designed to facilitate the bonding of the soft tissue support structure 12 to the bone ingrowth structure 14, as well as isolate the bone ingrowth structure from the soft tissue ingrowth structure, as will be described below.

Figure 2:
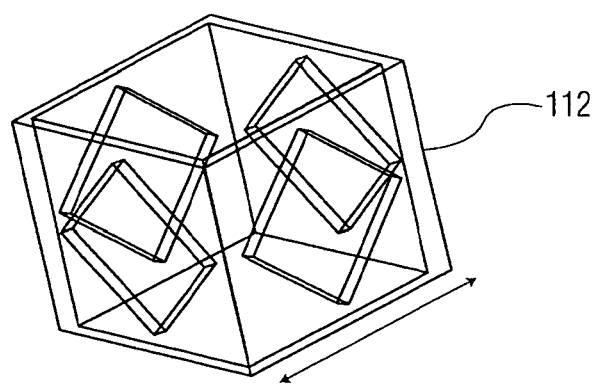
FIG. 2 is a repeating unit cell used to make the structure of FIG. 1.
Figure 3:
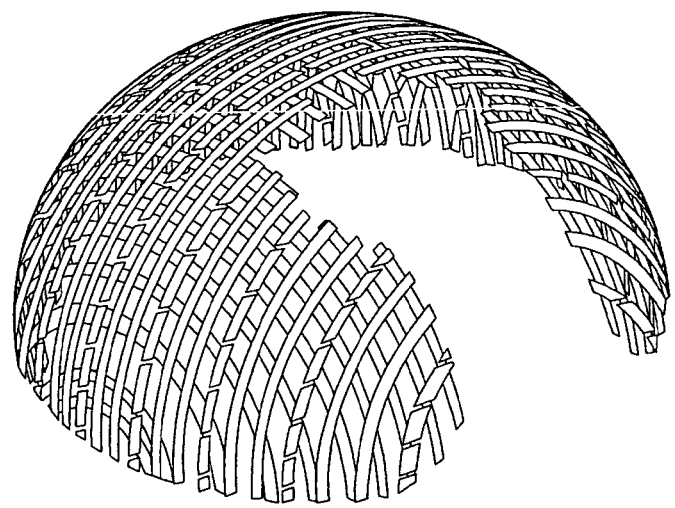
FIG. 3 is an implant made of the unit cells of FIG. 2.

The soft tissue ingrowth structure 12 may be designed by populating the volume of the structure with a single repeating unit cell 112, as shown in FIG. 2. This produces a structure that is between 80% to 95% porous with fully interconnected porosity with pore sizes between 0.1 mm and 2 mm diameter. Of course, the dimension of the unit cell 112 may be altered or even a difference unit cell employed, such that the porosity of the structure may be customized based on desirability.

The porosity of each structure may be altered but in a preferred embodiment the porosity of each structure is dependent on that structures function. Thus the resultant porosity of the bone ingrowth structure 14 should be within a range that promotes bone ingrowth. The porosity of the soft tissue ingrowth structure should be in a range that allows for soft tissue ingrowth. And the porosity of the intermediate layer should be in a range that prohibits or at least reduces the ability of soft tissue to extend from the soft tissue ingrowth structure 12 to the bone ingrowth structure 14 and vice versa.

Figure 4:
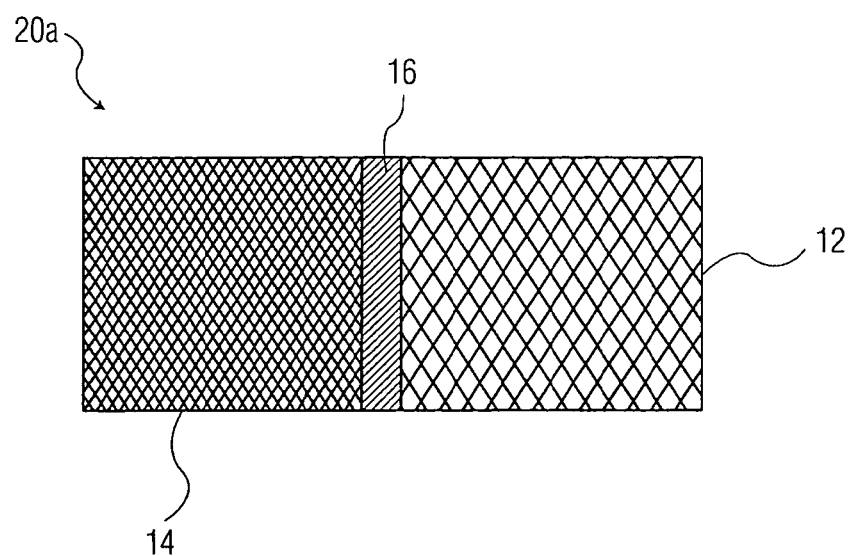
FIG. 4 is an alternate embodiment of the implant of FIG. 1.

The files describing the bone ingrowth structure 14, solid (fully dense) intermediate structure 16 and the tissue ingrowth structure 12 may all be loaded into the operating software for a MCP realizer, FUSCO. The three structures are then reassembled and manufactured as one part. A schematic of a manufactured part is shown in FIG. 4. Structure 20a includes a soft tissue attachment structure 12.

According to one method for forming a porous three-dimensional structure by laser melting, a powder of a magnesium/calcium alloy may be placed onto a substrate. The laser melting process includes scanning a laser beam onto the powder and in parallel scan lines with a beam overlap, e.g., scan spacing, followed by similar additional scans or subsequent scans at 90 degrees, as way of example. The type of scan chosen may depend on the initial layer thickness as well as the web height required. The web height refers to the height of a single stage of the metal structure 11. The web height may be increased by depositing additional layers of powder of a structure and scanning the laser at the same angle of the previous scan. Further, the additional scan lines may be at any angle to the first scan, to form a structure with the formation of a defined porosity, which may be regular or random. The scanned device may be programmed to proceed in a random generated manner to produce an irregular porous construct but with a defined level of porosity. Furthermore, the scan can be preprogrammed using digitized images of various structures, such as the acetabular cup 10, shown in FIGS. 1A and 1B, to produce a similar structure. The scan may also be customized to a particular patient. In this process, a CT scan of for instance, a person's acetabullum is taken and inputted into a computer program. The resultant file may be sliced, digitized or manipulated by methods known to those in the art as well as described herein. Based on these files and tailored measurements, a customized implant may be fabricated for a particular individual.

To produce a bone ingrowth structure, such as the bone ingrowth structure 14 of the acetabular cup 10, the nature of the material formed as a result of laser melting of powder beads is principally dependent upon the thermal profile involved (heating rate, soaking time, cooling rate); the condition of the raw material (size and size distribution of powder particles); atmospheric conditions (reducing, inert or oxidizing chamber gas); and accurate control of the deposited layer thickness.

The most optimum porous structure for maximization of bone in-growth on a prosthesis has generally been found to be between approximately 60% to 80%. Porous structure also can have both smaller interconnected pores and larger pores interconnected by the smaller pores. The preferred pore structure is irregular and interconnected, with a minimum interconnected pore size between about 80 µm and 100 µm and a maximum pore size of 800 µm. By pore size it is meant the average width of the pore.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant comprising:
   an entirely resorbable porous fused magnesium alloy powder bone ingrowth portion 1.4 to 1.6 mm thick made entirely of the resorbable magnesium alloy;
   a high density metal portion made entirely of a resorbable fused magnesium alloy powder having a first side fused to the porous bone ingrowth portion; and
   a porous metal soft tissue ingrowth portion entirely made of a resorbable fused magnesium alloy powder fused to a second side of the high density portion.

2. The implant as set forth in claim 1 wherein the high density portion has insufficient porosity to allow bone to migrate therethrough.

3. The implant as set forth in claim 1 wherein the high density portion is fully dense.

4. The implant as set forth in claim 1 where in the magnesium allow is a calcium magnesium alloy.

* * * * *